(12) United States Patent
Le Neve et al.

(10) Patent No.: US 10,314,867 B2
(45) Date of Patent: Jun. 11, 2019

(54) COMPOSITION FOR REDUCING INTESTINAL GAS PRODUCTION

(71) Applicant: COMPAGNIE GERVAIS DANONE, Paris (FR)

(72) Inventors: Boris Le Neve, Cachan (FR); Émilie Rocher, Massy (FR); Denis Guyonnet, Levallois Perret (FR)

(73) Assignee: COMPAGNIE GERVAIS DANONE, Paris (FR)

( * ) Notice: Subject to any disclaimer, the term of this patent is extended or adjusted under 35 U.S.C. 154(b) by 0 days.

(21) Appl. No.: 15/568,014

(22) PCT Filed: Apr. 23, 2015

(86) PCT No.: PCT/IB2015/052965
§ 371 (c)(1),
(2) Date: Oct. 20, 2017

(87) PCT Pub. No.: WO2016/170394
PCT Pub. Date: Oct. 27, 2016

(65) Prior Publication Data
US 2018/0133266 A1 May 17, 2018

(51) Int. Cl.
| | |
|---|---|
| *A61K 39/00* | (2006.01) |
| *A61K 39/02* | (2006.01) |
| *A01N 63/00* | (2006.01) |
| *A61K 35/745* | (2015.01) |
| *A61K 31/047* | (2006.01) |
| *A61K 31/7016* | (2006.01) |
| *A61K 31/702* | (2006.01) |
| *A61K 31/715* | (2006.01) |
| *A61K 31/718* | (2006.01) |
| *A61K 31/733* | (2006.01) |
| *A23L 33/135* | (2016.01) |
| *A61P 1/14* | (2006.01) |

(52) U.S. Cl.
CPC .......... *A61K 35/745* (2013.01); *A23L 33/135* (2016.08); *A61K 31/047* (2013.01); *A61K 31/702* (2013.01); *A61K 31/7016* (2013.01); *A61K 31/715* (2013.01); *A61K 31/718* (2013.01); *A61K 31/733* (2013.01); *A61P 1/14* (2018.01); *A23Y 2300/21* (2013.01)

(58) Field of Classification Search
CPC .......... A61K 39/00; A61K 39/02; A61K 39/09
USPC ................................................ 424/93.1, 93.4
See application file for complete search history.

(56) References Cited

U.S. PATENT DOCUMENTS

| | | | |
|---|---|---|---|
| 2011/0129451 A1* | 6/2011 | Guyonnet | A61K 35/74 424/93.44 |
| 2011/0182869 A1* | 7/2011 | Knol | A61K 35/74 424/93.45 |
| 2012/0315249 A1* | 12/2012 | Olmstead | A61K 45/06 424/93.3 |

FOREIGN PATENT DOCUMENTS

| | | |
|---|---|---|
| WO | WO 2009/150036 A1 | 12/2009 |
| WO | WO 2014/096901 A1 | 6/2014 |

OTHER PUBLICATIONS

"Guidance on the scientific requirements for health claims related to gut and immune function," European Food Safety Authority, EFSA Journal 2011; 9(4):1984, 2011.
Agrawal, A., et al., "Clinical trial: the effects of a fermented milk product containing bifidobacterium lactis DN-173?010 on abdominal distension and gastrointestinal transit in irritable bowel syndrome with constipation," Alimentary Pharmacology &Therapeutics, vol. 29, No. 1, pp. 104-114, Jan. 1, 2009.
Di Stefano, et al., "Non-absorbablew antibiotics for managing intestinal gas production and gas-related symptoms," Alimentary Pharmocology and Therapeutics, vol. 14, pp. 1001-1008, Apr. 2000.
International Search Report of related International Patent Application No. PCT/IB2015/052965 dated Oct. 21, 2015.
Rampengan, N.H., et al., "Comparison of Efficacies Between Live and Killed Probiotics in Children With Lactose Malabsorption," Southeast Asian J. Trop Med Public Health, vol. 41, No. 2, Mar. 2010.

* cited by examiner

*Primary Examiner* — Rodney P Swartz
(74) *Attorney, Agent, or Firm* — Arent Fox LLP

(57) ABSTRACT

The present invention relates to a composition comprising *Bifidobacterium* bacteria for use for reducing intestinal gas production in an individual.

17 Claims, 2 Drawing Sheets

COMPOSITION FOR REDUCING INTESTINAL GAS PRODUCTION

CROSS-REFERENCE TO RELATED APPLICATIONS

This application is a 35 U.S.C. 371 National Phase of International Patent Application No. PCT/IB2015/052965, filed on Apr. 23, 2015.

FIELD OF THE INVENTION

The present invention relates to a composition for use for reducing intestinal gas production in an individual.

TECHNICAL BACKGROUND

Excessive intestinal gas production is one of the causes of gastro-intestinal discomfort that can significantly affect well-being and quality of life. Gas-related symptoms are the most common and bothersome digestive symptoms, affecting 15-20% of the general population and up to 90% of patients suffering from irritable bowel syndrome (IBS). IBS patients or subgroups of IBS patients are generally considered an appropriate study group to substantiate claims on gastro-intestinal discomfort intended for the general population by the European Food Safety Authority (EFSA Journal 2011; 9(4):1984). No effective or sustainable treatments for excessive intestinal gas production are available today.

The major source of intestinal gas is the carbohydrate catabolic activity of colonic bacteria, which yields large volumes, mainly of hydrogen ($H_2$), but also of carbon dioxide ($CO_2$) and methane ($CH_4$).

One way to reduce intestinal gas production thus relies on diet restriction, by avoiding food containing fermentable substrates. However, not all fermentable substrates can be avoided and restrictive diets are difficult to comply with in the long run. In addition, long-term diets restricted in fermentable carbohydrates have marked effects on intestinal microbiota composition.

Accordingly, treatments by compounds which could diminish gas volume or production have emerged as an alternative. Simethicone and activated charcoal are among the most popular such treatments, but the few clinical studies devoted to these compounds have yielded contrasted, if not negative, results. In fact, to date, antibiotic treatments, e.g. with non-absorbable rifaximin, have proven the best way to reduce colonic gas production (see Di Stefano et al. (2000) *Aliment Pharmacol. Ther.* 14:1001-1008).

However, antibiotic usage is not devoid of side-effects and should be avoided whenever possible to limit the development of bacterial antibiotic resistance.

Accordingly, there is a need to find alternative ways of reducing colonic gas production.

SUMMARY OF THE INVENTION

The present invention arises from the unexpected discovery, by the present inventors, that oral administration of *Bifidobacterium* bacteria reduced intestinal gas in individuals, in particular in individuals having a high basal intestinal gas production.

Thus, the present invention relates to a composition comprising *Bifidobacterium* bacteria for use for reducing intestinal gas production in an individual.

The present invention also relates to the use of *Bifidobacterium* bacteria for the manufacture of a composition intended for reducing intestinal gas production in an individual. The present invention also relates to the use, in particular the non-therapeutic use, of a composition comprising *Bifidobacterium* bacteria for reducing intestinal gas production in an individual, in particular for alleviating at least one digestive symptom of the individual associated to intestinal gas production.

In a preferred embodiment of the invention, the above-defined composition further comprises at least one flatulogenic food. In such an embodiment, the *Bifidobacterium* bacteria are notably useful to reduce colonic intestinal gas production yielded by the consumption of the at least one flatulogenic food comprised in the composition.

The present invention also relates to a method for reducing intestinal gas production in an individual in need thereof, comprising administering an effective amount of a composition comprising *Bifidobacterium* bacteria to the individual.

The present invention also relates to a method for reducing intestinal gas production consecutive to the consumption of at least one flatulogenic food in an individual, comprising adding *Bifidobacterium* bacteria to the at least one flatulogenic food.

The present invention also provides a method for reducing intestinal gas production, comprising administering an effective amount of a composition comprising Bifidobacterium bacteria to the individual prior or subsequent to the consumption of at least one flatulogenic food.

The present invention also relates to products containing:
a composition comprising *Bifidobacterium* bacteria, and
at least one flatulogenic food,
as a combined preparation for simultaneous, separate or sequential use for reducing intestinal gas production in an individual, in particular intestinal gas production yielded by the consumption of the at least one flatulogenic food.

DETAILED DESCRIPTION OF THE INVENTION

Intestinal Gas production Reduction

As intended herein "intestinal gas production" relates to the production of gas by the intestinal microbiota, in particular the microbiota of the colon. Accordingly in one embodiment the present invention provides a composition comprising *Bifidobacterium* bacteria for use for reducing colonic gas production in an individual.

Intestinal gas production may be measured by determining the level, e.g. expressed in parts per million (ppm), of hydrogen ($H_2$) and/or methane ($CH_4$), in particular $H_2$, in the exhaled breath of the individual.

Exhaled breath $H_2$ and/or $CH_4$ levels can be determined by collecting end-expiratory breath samples in a system suitable for the sampling and storing of alveolar air, e.g. GaSampler System™, QuinTron Instrument Company, Milwaukee, Wis., and immediately analyzing them using a gas chromatograph, e.g. QuinTron Breath Tracker, QuinTron Instrument Company.

As intended herein, the "reduction" in intestinal gas production is with respect to gas production before administration or consumption of the composition comprising Bifidobacterium bacteria according to the invention. The reduction of intestinal gas production according to the invention is preferably at least 5%, more preferably at least 10% and most preferably at least 15%.

Preferably, the composition comprising *Bifidobacterium* bacteria according to the invention is used for preventing or treating at least one digestive symptom of the individual associated to intestinal gas production.

As intended herein, "digestive symptom" is considered a synonym of "gastro-intestinal (GI) symptom". The digestive symptom of the invention may be pathological or non-pathological. Preferably, the digestive symptom according to the invention is selected from the list consisting of excessive gas accumulation, flatulence, bloating, abdominal or intestinal or digestive discomfort, abdominal pain, abdominal distension, nausea, rumbling and urgency to have a bowel movement, more particularly from the list consisting of excessive gas accumulation, flatulence, bloating and abdominal distension.

Preferably also, the composition comprising *Bifidobacterium* bacteria according to the invention is used for reducing post-prandial or digestive intestinal gas production.

Individual

The "individual" according to the invention is preferably a mammal. In particular, it can be a farm animal such as a bovine, an ovine or a caprine, or a pet, such as a dog, a cat, a rabbit or a rodent. Most preferably, the individual according to the invention is a human.

The individual according to the invention may suffer from a digestive or gastro-intestinal disease or disorder. However, it is preferred that the individual according to the invention does not suffer from such a disease or disorder. In a particular embodiment of the invention, the individual is considered as being part of the general population or healthy.

Preferably, the individual according to the invention has above-normal or excessive basal intestinal gas production.

The term "basal" intestinal gas production notably relates to non-digestive intestinal gas production, i.e. intestinal gas production after a meal has been digested and before the next meal is ingested. Preferably, the basal intestinal gas production relates to intestinal gas production under fasting conditions, e.g. an overnight fast or a fast of at least 10 hours, preferably at least 12 hours.

An "above-normal" or "excessive" basal intestinal gas production relates to a basal intestinal gas production above the mean basal gas production of a random population of individuals. Preferably, the exhaled breath of the individual according to the invention comprises at least 7, 8, 9, 10, 11, 12, 13, 14 or 15 ppm $H_2$ under fasting conditions. Preferably also, the breath of the individual according to the invention comprises at the most 50, 40, 30 or 20 ppm $H_2$ under fasting conditions.

Composition

The present invention provides a composition comprising *Bifidobacterium* bacteria for use for reducing intestinal gas production in an individual. Preferably the *Bifidobacterium* bacterium is selected from the group consisting of *Bifidobacterium adolescentis, Bifidobacterium animalis, Bifidobacterium bifidum, Bifidobacterium breve, Bifidobacterium infantis,* or *Bifidobacterium longum* species. It is particularly preferred that the lactic acid bacterium according to the invention belongs to a *Bifidobacterium animalis* species. It is further preferred that the bacterium is *Bifidobacterium animalis* subsp. *lactis*. More preferably, the *Bifidobacterium animalis* bacteria comprised in the composition according to the invention belong to the strain deposited at the Collection Nationale de Culture de Microorganismes (CNCM, Paris, France) under the Budapest Treaty under reference CNCM I-2494.

In one embodiment, the composition according to the invention comprises at least $10^6$, more preferably at least $10^7$ and most preferably at least $10^8$ colony forming unit (CFU) of *Bifidobacterium* bacteria, more preferably *Bifidobacterium animalis*, according to the invention per gram (g) of composition according to the invention. Preferably also the composition according to the invention comprises up to about $10^{11}$, more preferably at least $10^{10}$ and most preferably at least $10^9$ colony forming unit (CFU) of *Bifidobacterium*, more preferably *Bifidobacterium animalis*, bacteria per gram (g) of composition according to the invention.

The composition according to the invention is suitable for consumption or ingestion, preferably by oral means. Accordingly the composition comprises or consists of comestible matter. It is particularly preferred that the compositions of the invention are substantially free of pathogenic or toxicogenic matter.

The composition according to the invention may be a pharmaceutical composition, a nutraceutical composition, and/or a food composition.

Where the composition according to the invention is a pharmaceutical composition it may also comprise at least one pharmaceutically acceptable excipient or vehicle.

Preferably, the composition according to the invention is a dairy composition, in particular a fermented dairy composition.

As intended herein, a "dairy composition" relates to a milk-based composition suitable for animal consumption, in particular human consumption. Preferably, the dairy composition according to the invention comprises or derives (in particular by fermentation) from a composition containing from 30 to 100% (w/w) milk, more preferably from 50 to 100% (w/w) milk and even more preferably from 70 to 100% (w/w) milk. As intended herein, the expression "x % (w/w)" is considered equivalent to "x g per 100 g". Preferably also, the dairy composition according to the invention comprises or derives (in particular by fermentation) from a composition essentially consisting of milk or consisting only of milk. As intended herein "milk" preferably relates to vegetal or animal milk, more preferably to soya, almond, oat, hemp, coconut, rice, goat, ewe, or cow milk and most preferably to cow milk.

Preferably, the dairy composition according to the invention comprises or derives (in particular by fermentation) from a composition comprising one or both of skimmed and non-skimmed milk. Preferably said milk or milks may be in liquid, powdered and/or concentrated form. In one embodiment said milk or milks may be enriched or fortified with further milk components or other nutrients such as but not limited to vitamins, minerals, trace elements or other micronutrients. Preferably, the dairy composition according to the invention is a fermented dairy composition, more preferably a fermented milk composition such as but not limited to a yogurt.

As intended herein, a "fermented dairy composition" is derived from a dairy composition according to the invention by the acidifying action of at least one lactic acid bacterium, which may be comprised in a ferment, a culture or a starter. More preferably said dairy composition according to the invention is obtained by the acidifying action of at least one, two, three, four, five, six, seven or more lactic acid bacteria strains. Accordingly the "fermented dairy composition" comprises at least one, two, three, four, five, six, seven or more lactic acid bacteria strains.

The lactic acid bacterium according to the invention preferably belongs to an Aerococcaceae, Carnobacteriaceae, Enterococcaceae, Lactobacillaceae, Leuconostocaceae, Streptococcaceae or Bifidobacteriaceae family and more preferably to an *Aerococcus, Carnobacterium, Enterococcus, Lactobacillus, Lactococcus, Leuconostoc, Oenococcus, Pediococcus, Streptococcus, Tetragenococcus, Vagococcus, Weissella* or *Bifidobacterium* genus. More preferably, the lactic acid bacterium according to the invention belongs to a *Lactobacillus brevis, Lactobacillus buchneri, Lactobacillus casei, Lactobacillus curvatus, Lactobacillus delbruckei,* in particular *L. delbruckei* supsb. *bulgaricus* or *lactis, Lactobacillus diolivorans, Lactobacillus fermentum, Lactobacillus fructivorans, Lactobacillus helveticus, Lactobacillus hilgardii, Lactobacillus jensenii, Lactobacillus kunkeei, Lactobacillus mall, Lactobacillus nagelii, Lactobacillus paracasei,* in particular

*L. paracasei* subsp. *paracasei, Lactobacillus plantarum, Lactobacillus vini, Lactobacillus rhamnosus, Streptococcus thermophilus, Streptococcus lactis, Streptococcus raffinolactis, Streptococcus cremoris, Bifidobacterium adolescentis, Bifidobacterium animalis, Bifidobacterium bifidum, Bifidobacterium breve, Bifidobacterium infantis, Bifidobacterium lactis,* or *Bifidobacterium longum* species. It is particularly preferred that the lactic acid bacterium according to the invention belongs to a *Bifidobacterium animalis* species. It is further preferred that the bacteria is of the *Bifidobacterium animalis* subspecies.

One or more lactic acid bacteria can be used for obtaining a fermented dairy composition according to the invention. Thus, in a preferred embodiment, a plurality of species of lactic acid bacteria comprising of *Streptococcus thermophilus* and *Lactobacillus delbrueckii* subsp. *bulgaricus* is used for obtaining a fermented dairy composition according to the invention. In a further embodiment, bacteria comprising of *Streptococcus thermophilus, Lactobacillus delbrueckii* subsp. *bulgaricus, Bifidobacterium* and *Lactococcus* are used for obtaining a fermented dairy composition according to the invention. Accordingly in one embodiment the invention provides a fermented dairy composition comprising of *Streptococcus thermophilus* and *Lactobacillus delbrueckii* subsp. *bulgaricus,* which in a further embodiment may additionally comprise *Bifidobacterium* and *Lactococcus* bacteria.

In a preferred embodiment, the lactic acid bacterium is a probiotic bacterium. The expressions "fermented milk" and "yogurt" have the usual meanings attributed to them and may in appropriate circumstances be used interchangeably, e.g. a fermented dairy composition comprising *Lactobacillus bulgaricus, Streptococcus thermophilus* and further additional bacteria (e.g. probiotic strains) may be referred to as a "fermented milk" or alternatively as "yogurt".

Methods for the preparation of fermented milk products, such as yogurts or equivalents thereof, are well-known in the art. Typically a fermented milk product is prepared by culture of heat-treated (e.g. pasteurized) skimmed and/or non-skimmed milks with suitable microorganisms to provide a reduction in pH. The selection of suitable microorganisms (e.g. thermophilic lactic acid bacteria) is within the scope of the skilled person and for the preparation of yogurt will typically include *Lactobacillus bulgaricus* (also referred to as *Lactobacillus delbrueckii* subsp. *bulgaricus*) and *Streptococcus thermophilus,* optionally with additional microorganisms such as but not limited to probiotic species or other species that may provide desirable organoleptic qualities to the composition.

The dairy composition, in particular the fermented dairy composition, according to the invention, may optionally further comprise secondary ingredients such as fruits, vegetables, nutritive and non-nutritive sweeteners, cereals, flavours, starch, thickeners, preservatives or stabilizers. Preferably the dairy composition, in particular the fermented dairy composition, according to the invention shall comprise up to about 30% (w/w) of said secondary ingredients, e.g. up to about 10%, 15%, 20%, 25% (w/w).

Preferably the dairy composition according to the invention is a fermented dairy composition, more preferably a fermented milk composition that comprises, comprises essentially or consists of milk that has been subjected to heat treatment at least equivalent to pasteurization, preferably said heat treatment is carried out prior to the preparation of the dairy composition or fermented dairy composition.

Preferably the dairy composition according to the invention is a fermented dairy composition, more preferably a fermented milk composition that comprises above about 0.3 g per 100 g by weight free lactic acid, more preferably the invention provides a fermented milk composition comprising above about 0.7 g or 0.6 g per 100 g by weight free lactic acid. Preferably the dairy composition according to the invention is a fermented dairy composition, more preferably a fermented milk composition that comprises a protein content at least equivalent to that of the milk or milks from which it is derived.

Preferably the dairy composition according to the invention is a fermented dairy composition, more preferably a fermented milk composition that has a pH equal to or lower than 5, more preferably between about 3.5 and about 4.5.

Preferably the dairy composition according to the invention is a fermented dairy composition, more preferably a fermented milk composition that has a viscosity lower than 200 mPa·s, more preferably lower than 100 mPa·s and most preferably lower that 60 mPa·s, at 10° C., at a shear rate of 64 s$^{-1}$. In one embodiment the dairy composition according to the invention is a drinkable fermented dairy composition, more preferably a fermented milk drink such as but not limited to a yogurt drink, kefir etc. In an alternative embodiment the dairy composition according to the invention is a fermented dairy composition, more preferably a fermented milk composition that is spoonable. As used herein the term "spoonable" shall be taken to mean a solid or semi-solid that may be consumed by means of a spoon or other utensil.

Preferably also, the dairy composition, in particular the fermented dairy composition, according to the invention, or the product according to the invention, may be stored at a temperature of from 1° C. to 10° C.

A single serving portion of the dairy composition, in particular the fermented dairy composition according to the invention, more preferably a fermented milk composition or the product according to the invention is preferably about 50 g, 60 g, 70 g, 75 g, 80 g, 85 g, 90 g, 95 g, 100 g, 105 g, 110 g, 115 g, 120 g, 125 g, 130 g, 135 g, 140 g, 145 g, 150 g, 200 g, 300 g or 320 g or alternatively about 1 oz, 2 oz, 3 oz, 4 oz, 5 oz, 6 oz or 12 oz by weight.

It is particularly preferred that the dairy composition, in particular the fermented dairy composition according to the invention, more preferably a fermented milk composition comprise *Bifidobacterium* bacteria. Preferably, the *Bifidobacterium* bacteria comprised in the dairy composition, in particular the fermented dairy composition according to the invention, more preferably a fermented milk composition according to the invention belong to the animalis species. It is further preferred that the bacterium is *Bifidobacterium animalis* subspecies *lactis*. More preferably, the *Bifidobacterium animalis* bacteria comprised in the dairy composition, in particular the fermented dairy composition according to the invention, more preferably a fermented milk composition according to the invention belong to the strain deposited at the Collection Nationale de Culture de Microorganismes (CNCM, Paris, France) under the Budapest Treaty under reference CNCM I-2494.

Preferably, the dairy composition, in particular the fermented dairy composition according to the invention, more preferably a fermented milk composition according to the invention comprises at least $10^6$, more preferably at least $10^7$ and most preferably at least $10^8$ colony forming unit (CFU) of *Bifidobacterium* bacteria according to the invention per gram (g) of composition according to the invention. Preferably also the composition according to the invention comprises up to about $10^{11}$, more preferably at least $10^{10}$ and most preferably at least $10^9$ colony forming unit (CFU) of *Bifidobacterium* bacteria according to the invention per gram (g) of composition according to the invention.

Preferably, the dairy composition, in particular the fermented dairy composition according to the invention, more preferably a fermented milk composition according to the invention comprises at least $10^6$, more preferably at least $10^7$ and most preferably at least $10^8$ colony forming unit (CFU) of *Lactobacillus bulgaricus* (also referred to as *Lactobacillus delbrueckii* subsp. *bulgaricus*) and *Streptococcus thermophilus*, according to the invention per gram (g) of composition according to the invention e.g. at least of $5\times10^6$ *Lactobacillus bulgaricus* and $5\times10^6$ *Streptococcus thermophilus*. Preferably also the composition according to the invention comprises up to about $10^{11}$, more preferably at least $10^{10}$ and most preferably at least $10^9$ colony forming unit (CFU) of *Lactobacillus bulgaricus* (also referred to as *Lactobacillus delbrueckii* subsp. *bulgaricus*) and *Streptococcus thermophilus* bacteria per gram (g) of composition according to the invention.

Methods for the preparation of fermented milk products, such as yogurts or equivalents thereof, are well-known in the art. Typically a fermented milk product is prepared by culture of heat-treated (e.g. pasteurized) skimmed and/or non-skimmed milks with suitable microorganisms to provide a reduction in pH. The selection of suitable microorganisms (e.g. thermophilic lactic acid bacteria) is within the scope of the skilled person and for the preparation of yogurt will typically include *Lactobacillus bulgaricus* (also referred to as *Lactobacillus delbrueckii* subsp. *bulgaricus*) and *Streptococcus thermophilus*, optionally with additional microorganisms such as but not limited to probiotic species and/or other species that may provide desirable organoleptic qualities to the composition. Fermented milk products may be either or set or stirred subsequent to culture.

Flatulogenic Food

As intended herein, a "flatulogenic food" relates to a food which upon ingestion leads to intestinal gas production, in particular significant intestinal gas production or intestinal gas production yielding at least one digestive or gastrointestinal symptom, such as excessive gas accumulation, flatulence, bloating or abdominal distension.

Preferably, the composition according to the invention is used for reducing intestinal gas production consecutive to consumption of flatulogenic food. In one embodiment said flatulogenic food is comprised in the composition according to the invention. In an alternative embodiment the present invention provides a method for reducing intestinal gas production prior to or subsequent to the consumption of at least one flatulogenic food in an individual, comprising administering an effective amount of a composition comprising *Bifidobacterium* bacteria to the individual prior to or subsequent to the consumption of at least one flatulogenic food. In a further alternative embodiment the present invention provides the use of a composition comprising *Bifidobacterium* bacteria for reducing intestinal gas production prior to or subsequent to the consumption of at least one flatulogenic food in an individual.

Preferably, the flatulogenic food according to the invention comprises or consists of at least one fermentable ingredient, such as a carbohydrate. Preferably, the flatulogenic food according to the invention comprises or consists of at least one ingredient selected from the list consisting of an α-galactoside, a monosaccharide, a disaccharide, a polysaccharide, an oligosaccharide, a polyol, a fiber, a cellulose, a pectin. More preferably the flatulogenic food according to the invention comprises or consists of at least one ingredient selected from the group consisting of lactulose, lactose, fructose, xylose, arabinose, fructans, stachyose, raffinose, melibiose, manninotriose, inuline, starch, sorbitol, mannitol, xylitol.

Dosage Regimens

In one embodiment the present invention provides the consumption or administration of a dose of between about $10^8$ and about $10^{11}$ colony forming unit (CFU) of *Bifidobacterium* bacteria, preferably between about $10^8$ and about $10^9$, more preferably between about $10^9$ and about $10^{10}$ colony forming unit (CFU) and in an alternative embodiment between about $10^{10}$ and about $10^{11}$ colony forming unit (CFU) of *Bifidobacterium* bacteria, more preferably *Bifidobacterium animalis*. In a further embodiment at least 1, 2, 3, or 4 doses are provided within a 24 hour time period. It is further preferred that the daily dosage regimen is maintained for at least about 1, 2, 3, 4, 5, 6 or 7 days, or in alternative embodiment for at least about 1, 2, 3, 4, 5, 6 or 7 weeks.

Accordingly, in one embodiment the present invention provides the daily consumption or administration of at least 1, 2, 3, or 4 servings of the dairy composition, in particular the fermented dairy composition according to the invention, more preferably a fermented milk composition according to the invention, or the product according to the invention. Each serving may be consumed or administered individually, or a plurality of servings may be consumed or administered in a single instance. Each of said servings may be consumed at mealtimes or between mealtimes (e.g. as a snack, subsequent to sporting activities etc. . . . ).

A single serving portion of the dairy composition, in particular the fermented dairy composition according to the invention, more preferably a fermented milk composition, according to the invention, or the product according to the invention is preferably about 50 g, 60 g, 70 g, 75 g, 80 g, 85 g, 90 g, 95 g, 100 g, 105 g, 110 g, 115 g, 120 g, 125 g, 130 g, 135 g, 140 g, 145 g, 150 g, 200 g, 300 g or 320 g or about 1 oz, 2 oz, 3 oz, 4 oz, 5 oz, 6 oz or 12 oz by weight.

Preferably, the composition according to the invention comprises at least $10^6$, more preferably at least $10^7$ and most preferably at least $10^8$ colony forming unit (CFU) of *Bifidobacterium* bacteria, more preferably *Bifidobacterium animalis*, according to the invention per gram (g) of composition according to the invention. Preferably also, the composition according to the invention comprises at least $10^{11}$, more preferably at least $10^{10}$ and most preferably at least $10^9$ colony forming unit (CFU) of *Bifidobacterium*, more preferably *Bifidobacterium animalis*, bacteria per gram (g) of composition according to the invention.

For example, in one embodiment the present invention provides the daily consumption of at least 2 or at least 3 servings of a 100 g or 125 g portion of a fermented milk product (such as a product sold under the brand name Activia®) comprising between about at least $10^7$ and at least $10^8$ colony forming units (CFU) *Bifidobacterium animalis* bacteria per g of product. In a further embodiment said daily level of consumption is maintained over a period of at least 1, 2, 3, 4 or more weeks.

Kits

In a further embodiment the present invention provides a kit (i.e., article of manufacture) for the herein disclosed uses of the compositions of the invention, said kit comprising:

i) A receptacle containing a composition according to the invention comprising *Bifidobacterium*, and ii) Printed matter disclosing that said compositions may be of use in reducing intestinal or colonic gas production.

In a preferred embodiment said composition comprises between about $10^8$ and about $10^{19}$ colony forming unit (CFU) of *Bifidobacterium* bacteria, preferably between about $10^8$ and about $10^9$ and more preferably between about $10^9$ and about $10^{10}$ colony forming unit (CFU) of *Bifidobacterium* bacteria, more preferably *Bifidobacterium animalis*.

Preferably the printed matter may be in the form of a label or packaging insert.

In an additional embodiment the invention further provides a kit (i.e., article of manufacture) comprising:

i) a composition comprising *Bifidobacterium animalis* bacteria, and ii) at least one flatulogenic food, as a combined preparation for simultaneous, separate or sequential use for reducing intestinal gas production in an individual, in particular intestinal gas production yielded by the consumption of the at least one flatulogenic food.

The invention will be further illustrated by the following non-limitative Figures and Example.

EXAMPLE

Figure 1:
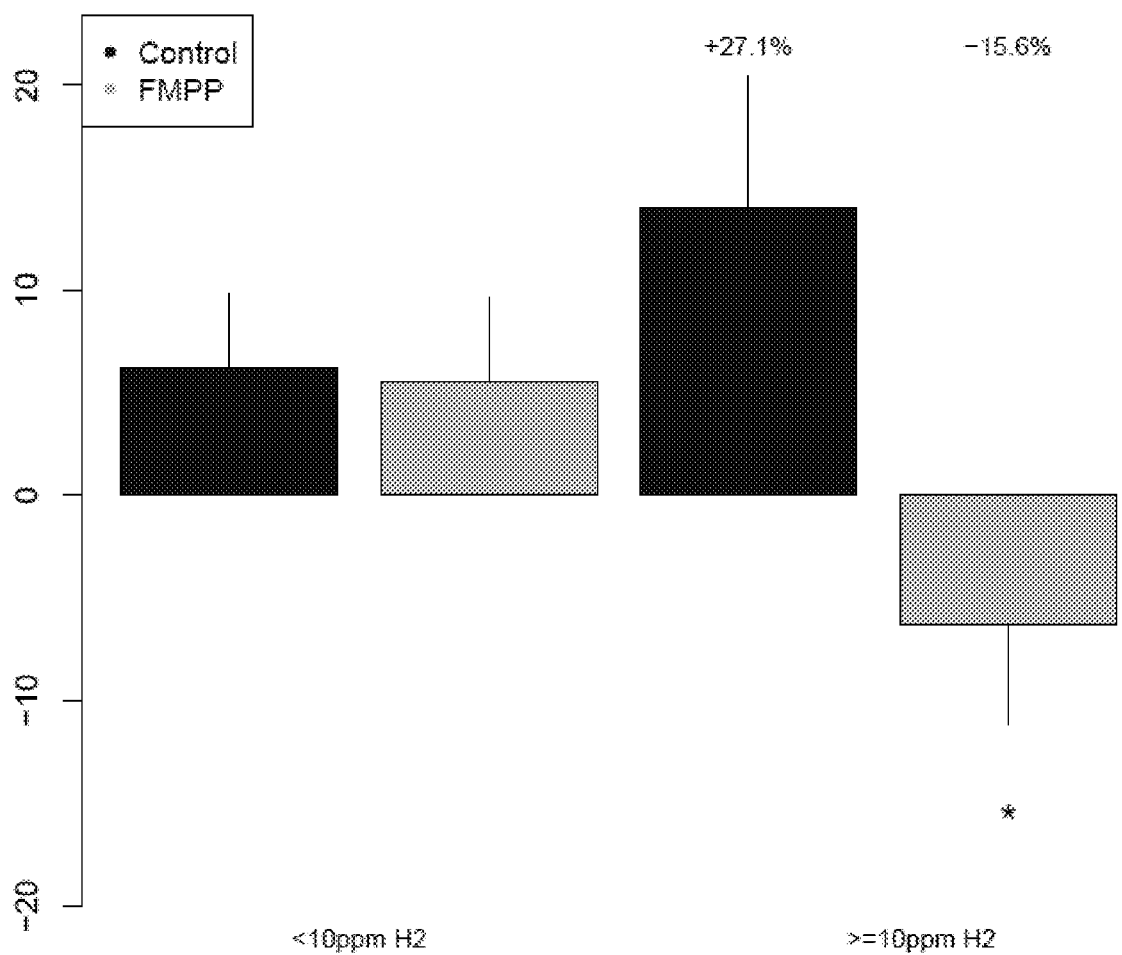
FIG. 1 represents the mean change in hydrogen ($H_2$) breath levels (vertical axis, in ppm) elicited by consumption of lactulose in subjects which have a basal $H_2$ breath level of at least 10 ppm (right panel), and in subjects which have a basal breath level of less than 10 ppm (left panel). The change is the difference between $H_2$ breath levels after and before consumption of a control composition (control; left bar of each panel; black) or the test composition (Fermented Milk Product with Probiotic (FMPP); right bar of each panel; grey).

Material and Methods
Subjects and Study Design

IBS patients or subgroups of IBS patients are generally considered an appropriate study group to substantiate claims on gastro-intestinal discomfort intended for the general population by the European Food Safety Authority (EFSA Journal 2011; 9(4):1984). All participants were subjected to a combined nutrient and lactulose challenge test for the assessment of gastrointestinal symptoms and the amount of exhaled H2 as objective marker of intestinal gas production. Adult subjects fulfilling Rome III criteria for irritable bowel syndrome (IBS) were prospectively included at a tertiary care outpatient clinic. The diagnosis was based on a typical clinical presentation and additional investigations if considered necessary. Classification into IBS subtypes according to Rome III criteria was done based on Bristol Stool Form scale characteristics: IBS with constipation (IBS-C), IBS with diarrhea (IBS-D), mixed IBS (IBS-M) or unsubtyped IBS (IBS-U) (Table 1). All participants, aged between 18 and 65 years at inclusion visit, gave their written informed consent and were allowed to withdraw from the study at any time. Exclusion criteria included the use of probiotics or antibiotics during the study or within one month before the inclusion, severe psychiatric disease and history of drug or alcohol abuse.

The study was a single centre, randomized, double-blind and controlled parallel-group design in which 100 subjects consumed (125g/serving) twice a day either the test composition or a control composition for 14 days. The test composition was a fermented milk, containing *Bifidobacterium animalis* deposited at the Collection Nationale de Culture de Microorganismes (CNCM, Paris, France) under the Budapest Treaty under reference CNCM I-2494 (1.25× $10^{10}$ colony forming unit (cfu) per serving) together with the two classical yoghurt starters, *S. thermophilus* and *L. bulgaricus* (1.2×$10^9$ cfu/serving). The test composition was unflavoured. The control composition was a milk-based non-fermented dairy product without probiotics and with low content of lactose<4 g/pot (as in the test composition). Each serving of either test or control composition contained 125 g.

A lactulose challenge test (see below) was performed in all subjects prior to and following the intervention period of 14 days.

TABLE 1

| Clinical characteristics at baseline for study subjects. | |
|---|---|
| Mean (95% CI) | IBS (n = 100) |
| Age (range) | 34.4 (32.1-36.7) |
| Gender (F/M) | 61/28 |
| BMI | 23.0 (22.4-23.7) |
| IBS-C (n) | 19 |
| IBS-D (n) | 32 |
| IBS-M (n) | 35 |
| IBS-U (n) | 14 |
| PI-IBS (n) | 17 |

BMI: body mass index; IBS-C: irritable bowel syndrome with constipation; IBS-D: irritable bowel syndrome with diarrhea; IBS-M: irritable bowel syndrome with mixed pattern; IBS-U: irritable bowel syndrome unsubtyped; PI-IBS: post-infectious IBS.

Lactulose Challenge Test

All participants arrived to the laboratory in the morning (7:30-8:00 a.m.) after an overnight fast. They had been instructed to avoid consumption of food containing dietary fibers the day before the test. The lactulose challenge test meal (400 ml Nutridrink®, 1.5 kcal/ml, 16% proteins, 49% carbohydrates, 35% fat, gluten free, lactose<0.025 g/100 ml, combined with 25 g of lactulose) was served at 8:00 a.m. The 25 g lactulose dose was chosen according to the outcome of our previous pilot study (Le Nevé et al. (2013) *Am J Gastroenterol.* 108(5):786-95). The severity of eight GI symptoms, the overall digestive comfort and the amount of exhaled $H_2$ as objective marker of intestinal gas production were assessed every 15 min starting 30 min before the test meal and during 4 h following meal intake. The amount of exhaled $H_2$ was measured in parts per million (ppm). All breath samples were end-expiratory, collected in a system used for the sampling and storing of alveolar air (GaSampler system, QuinTron Instrument Company, Milwaukee, Wis., USA) and analyzed immediately using a gas chromatograph (QuinTron Breath Tracker, QuinTron Instrument Company, Milwaukee, Wis., USA).

Questionnaires

The severity of eight GI symptoms (flatulence, bloating, abdominal discomfort, abdominal distension, nausea, stomach rumbling, abdominal pain and urgency to have a bowel movement) and the level of digestive comfort were assessed at baseline (T0) and every 15 min during the lactulose challenge test using 20-point numerical rating scales, with 0 corresponding to "no sensation" and 20 corresponding to "the most intense sensation imaginable" for the symptoms, and with 0 corresponding to "extremely uncomfortable", 10 corresponding to "neutral" and 20 corresponding to "extremely comfortable" for digestive comfort.

Statistical Analysis

A classification of the study subjects was made before the ingestion of the test meal containing lactulose during the first lactulose challenge test. The classification of subjects was made considering a cut-off at 10 ppm for basal $H_2$ breath levels. Subjects with a basal production of $H_2$ lower than 10 ppm were considered normal $H_2$ producers whereas subjects with a basal production of $H_2$ equal to or higher than 10 ppm were considered high $H_2$ producers. Table 2 represents the repartition of study subjects during the intervention between groups according to this basal $H_2$ breath level classification.

TABLE 2

Contingency table between basal $H_2$ breath level classification of subjects and intervention groups

|  | Test composition | Control composition |
| --- | --- | --- |
| basal $H_2$ breath level <10 ppm | 29 | 38 |
| basal $H_2$ breath level ≥10 ppm | 21 | 12 |

The change of each parameter: severity of 8 individual GI symptoms, composite score of 8 GI symptoms, level of digestive comfort, exhaled $H_2$, was evaluated by an Analysis Of Variance (ANOVA) model taking into account three factors:

Intervention group: "test composition" or "control composition"

Basal $H_2$ breath level: "<10 ppm $H_2$" or "≥10 ppm $H_2$"

Interaction between intervention group and basal $H_2$ breath level

The significance of the main effects "intervention group" and "basal $H_2$ breath level" were evaluated at a 0.05 significance level. The interactions between "intervention group" and "basal $H_2$ breath level" were evaluated at a 0.10 significance level. Least squares means comparison was done on the interaction between "intervention group" and "basal $H_2$ breath level" only if this interaction was significant at the defined threshold. For parameters where the interaction was statistically significant, least squares means comparison was also done on "intervention group" even if this main effect was not statistically significant to evaluate the magnitude of the effects in each "basal $H_2$ breath level" compared to the global population. The equality of variance in each group was assessed by the test of Bartlett. The normality of the residuals was assessed by kurtosis and skewness values. The kurtosis and skewness values had to be in the range of [−2, 2]. The main parameter considered was the equality of variance in each group. In case the equality of variance was verified but not the normality of residuals, a non-parametric Kruskall Wallis test was performed to confirm the results, but the ANOVA model results were kept if both outcomes had the same significativity.

Results

The inventors classified the study subjects in two groups (see statistical section above):

A basal high $H_2$ producer group (n=33, $n_{test}$=21, $n_{control}$=12), with at least 10 ppm breath $H_2$ before ingestion of the test meal comprising lactulose;

A basal low $H_2$ producer group (n=67, $n_{test}$=29, $n_{control}$=38), with less than 10 ppm breath $H_2$ before ingestion of the test meal comprising lactulose.

Figure 2:
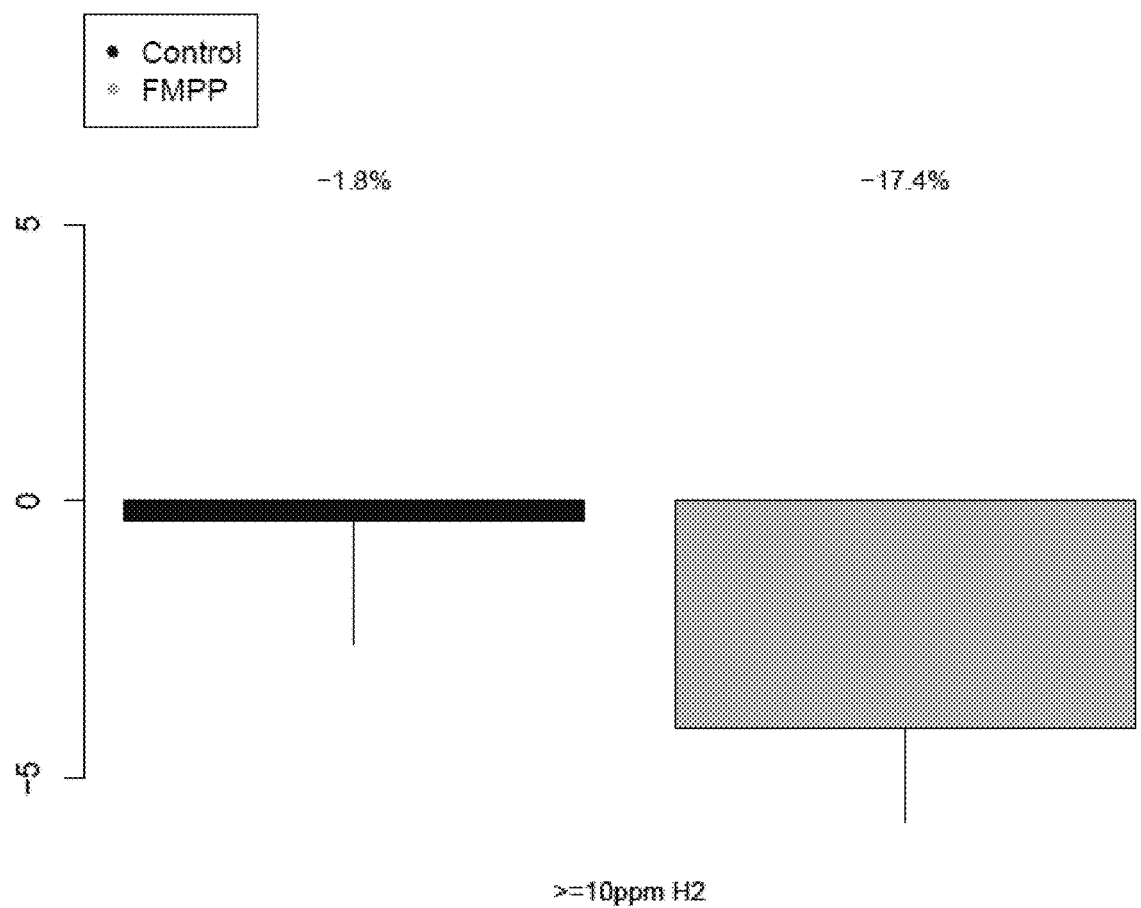
FIG. 2 represents the mean change in the composite score of eight (8) gastro-intestinal (GI) symptom levels (vertical axis, numerical score) elicited by consumption of lactulose in subjects which have a basal $H_2$ breath level of at least 10 ppm (right panel). The change is the difference between the composite score of 8 GI symptoms after and before consumption of a control composition (control; left bar; black) or the test composition (FMPP; right bar; grey).

Changes in breath $H_2$ and in gastro-intestinal (GI) symptoms elicited by a lactulose challenge test before and after intervention (i.e. consumption of the test composition or the control composition) are shown in FIGS. 1-2.

Briefly, in basal high $H_2$ producers, intestinal gas production following a lactulose challenge test was significantly reduced by the consumption of the test composition as compared to the control composition. This is evidenced by a reduction in mean breath $H_2$ of 15.6%. In contrast, no such reduction of intestinal gas production could be evidenced in subjects with basal low $H_2$ production (FIG. 1).

This effect on intestinal gas production was paralleled by a decrease in the severity of the eight gastro-intestinal (GI) symptoms for subjects with basal high $H_2$ production. This is evidenced by a reduction in the mean composite score for the eight GI symptoms of 17.4% in basal high $H_2$ producers consuming the test composition as compared to the control composition (see FIG. 2).

The invention claimed is:

1. A method for reducing intestinal gas production in an individual comprising administering a composition comprising *Bifidobacterium animalis* bacteria to the individual, wherein the individual's exhaled breath comprises at least 10 ppm $H_2$ under fasting conditions.

2. The method of claim 1, further comprising administering the *Bifidobacterium animalis* bacteria prior to, with, or subsequent to consumption of a flatulogenic food by the individual.

3. The method according to claim 1, wherein the *Bifidobacterium animalis* bacteria belong to the *Bifidobacterium animalis* subspecies *lactis*.

4. The method according to claim 1, wherein the *Bifidobacterium animalis* bacteria belong to the strain deposited under reference number CNCM I-2494.

5. The method according to claim 1, wherein the composition is a dairy composition.

6. The method according to claim 5, wherein the dairy composition is a fermented dairy composition.

7. The method according to according to claim 1, wherein the composition further comprises at least one flatulogenic food.

8. The method according to claim 7, wherein the flatulogenic food comprises at least one ingredient of lactulose, lactose, fructose, xylose, arabinose, fructans, stachyose, raffinose, melibiose, manninotriose, inuline, starch, sorbitol, mannitol, or xylitol.

9. The method according to claim 1, further comprising administering the *Bifidobacterium animalis* bacteria prior to consumption of a flatulogenic food by the individual.

10. The method according to claim 1, further comprising administering the *Bifidobacterium animalis* bacteria subsequent to consumption of a flatulogenic food by the individual.

11. The method according to claim 2, wherein the flatulogenic food comprises at least one ingredient of lactulose, lactose, fructose, xylose, arabinose, fructans, stachyose, raffinose, melibiose, manninotriose, inuline, starch, sorbitol, mannitol, or xylitol.

12. The method according to claim 1, further comprising treating at least one digestive symptom of the individual associated with intestinal gas production.

13. The method according to claim 1, wherein the intestinal gas is post-prandial or digestive intestinal gas.

14. The method according to claim 1, wherein the composition comprises from $10^8$ and to $10^{11}$ colony forming unit (CFU) of the *Bifidobacterium animalis* bacteria.

15. The method according to claim 14, further comprising administering the composition at least once daily for at least 1, 2, 3, or 4 weeks.

16. The method of claim 1, wherein the composition is a fermented dairy composition and comprises from $10^8$ and to $10^{11}$ CFU of the *Bifidobacterium animalis*, and further comprising administering the composition at least once daily.

17. The method of claim 16, wherein the composition further comprises *Lactobacillus bulgaricus* and *Streptococcus thermophilus*.

* * * * *